(12) United States Patent
Wagner

(10) Patent No.: US 9,144,512 B2
(45) Date of Patent: Sep. 29, 2015

(54) ORAL DEVICES, KITS, AND METHODS FOR REDUCING SLEEP APNEA, SNORING, AND/OR NASAL DRAINAGE

(75) Inventor: Wayne R. Wagner, The Woodlands, TX (US)

(73) Assignee: W. R. WAGNER FAMILY LIMITED PARTNERSHIP, Houston, TX (US)

( * ) Notice: Subject to any disclaimer, the term of this patent is extended or adjusted under 35 U.S.C. 154(b) by 251 days.

(21) Appl. No.: 13/456,682

(22) Filed: Apr. 26, 2012

(65) Prior Publication Data
US 2013/0284184 A1     Oct. 31, 2013

Related U.S. Application Data

(60) Provisional application No. 61/488,021, filed on May 19, 2011.

(51) Int. Cl.
*A61F 5/56* (2006.01)

(52) U.S. Cl.
CPC ..................... *A61F 5/566* (2013.01)

(58) Field of Classification Search
USPC ............... 128/857, 859–862, 848; 433/6–7
See application file for complete search history.

(56) References Cited

U.S. PATENT DOCUMENTS

| | | | |
|---|---|---|---|
| 4,396,373 A * | 8/1983 | Dellinger | 433/19 |
| 4,700,697 A | 10/1987 | Mundell et al. | |
| 4,708,646 A | 11/1987 | Jasper | |
| 4,901,737 A | 2/1990 | Toone | |
| 5,239,995 A | 8/1993 | Estes et al. | |
| 5,499,633 A | 3/1996 | Fenton | |
| RE35,295 E | 7/1996 | Estes et al. | |
| 5,570,704 A | 11/1996 | Buzzard et al. | |
| 5,611,355 A | 3/1997 | Hilsen | |

(Continued)

FOREIGN PATENT DOCUMENTS

| | | | |
|---|---|---|---|
| EP | 1205157 A1 | 5/2002 | |
| WO | 2007134375 A1 | 11/2007 | |

(Continued)

OTHER PUBLICATIONS

Landers, SJ, "Link strengthened between sleep apnea and mortality risk", amednews, Sep. 1, 2008.

(Continued)

*Primary Examiner* — Ophelia A Hawthorne
(74) *Attorney, Agent, or Firm* — Jeffrey L. Wendt; The Wendt Firm, P.C.

(57) ABSTRACT

Apparatus for reducing obstructive sleep apnea, snoring and/or nasal drainage. One apparatus includes an upper member fitting the interior and exterior surfaces of a user's upper dentition, and a lower member fitting similarly adjacent a user's lower dentition. The lower member includes molar extensions projecting away from the lower member. The upper member includes upper molar extensions projecting away from the upper member and toward the lower molar extensions so that when the user bites or clenches, the upper right and lower right extensions impinge on one another in substantially overlapping fashion, as do the molar upper left and lower left extensions. The upper and lower members have an anterior shape to form a gap sufficient for the user's tongue to extend into the gap, and each molar extension may include a magnet. Methods of using the apparatus and kits to reduce sleep apnea, snoring, and/or nasal drainage.

3 Claims, 9 Drawing Sheets

(56) References Cited

U.S. PATENT DOCUMENTS

| | | | |
|---|---|---|---|
| 5,692,521 | A | 12/1997 | Leasure-Nelson |
| 6,074,207 | A | 6/2000 | Coats |
| 6,082,363 | A | 7/2000 | Washburn |
| 6,109,265 | A | 8/2000 | Frantz et al. |
| 6,213,959 | B1 | 4/2001 | Kushida |
| 6,427,689 | B1 | 8/2002 | Estes et al. |
| 6,505,625 | B1 | 1/2003 | Uenishi |
| 6,766,802 | B1 | 7/2004 | Keropian |
| 7,107,992 | B2 | 9/2006 | Brooks et al. |
| 7,178,529 | B2 | 2/2007 | Kownacki |
| 7,225,021 | B1 | 5/2007 | Park et al. |
| 7,255,110 | B2 | 8/2007 | Knudson et al. |
| 7,322,356 | B2 | 1/2008 | Critzer et al. |
| 7,451,767 | B2 | 11/2008 | Keropian |
| 7,540,843 | B2 | 6/2009 | De Backer |
| 7,607,439 | B2 | 10/2009 | Li |
| 7,637,262 | B2 * | 12/2009 | Bailey .......................... 128/848 |
| 7,712,468 | B2 | 5/2010 | Hargadon |
| 7,810,502 | B1 | 10/2010 | Nguyen et al. |
| 8,215,312 | B2 * | 7/2012 | Garabadian et al. .......... 128/848 |
| 2001/0027793 | A1 | 10/2001 | Tielemans |
| 2004/0177852 | A1 | 9/2004 | Abramson |
| 2005/0121039 | A1 | 6/2005 | Brooks et al. |
| 2005/0236003 | A1 | 10/2005 | Meader |
| 2006/0252685 | A1 | 11/2006 | Gould |
| 2006/0289013 | A1 | 12/2006 | Keropian |
| 2007/0283967 | A1 | 12/2007 | Bailey |
| 2008/0060660 | A1 | 3/2008 | Nelson et al. |
| 2008/0173312 | A1 | 7/2008 | Peake et al. |
| 2008/0199824 | A1 | 8/2008 | Hargadon |
| 2008/0210244 | A1 | 9/2008 | Keropian |
| 2008/0257358 | A1 | 10/2008 | Stern et al. |
| 2008/0264422 | A1 | 10/2008 | Fishman |
| 2008/0276938 | A1 | 11/2008 | Jeppesen et al. |
| 2009/0036889 | A1 | 2/2009 | Callender |
| 2009/0056724 | A1 | 3/2009 | Keropian |
| 2009/0120448 | A1 | 5/2009 | Keropian |
| 2009/0188510 | A1 | 7/2009 | Palmer |
| 2010/0211184 | A1 | 8/2010 | Rousseau et al. |
| 2010/0224197 | A1 | 9/2010 | Keropian |
| 2010/0300458 | A1 * | 12/2010 | Stubbs et al. ................. 128/848 |

FOREIGN PATENT DOCUMENTS

| | | | |
|---|---|---|---|
| WO | 2010040026 | A1 | 4/2010 |
| WO | 2010062952 | A1 | 6/2010 |
| WO | 2010093264 | | 8/2010 |

OTHER PUBLICATIONS

Sleep Apnea Appliances, I Hate CPAP!, pp. 1-8, downloaded from the Internet Oct. 25, 2010.

Prehn, Ronald S., "What is a Mandibular Advancement Splint and How Does it Work?", YouTube video, uploaded to the Internet by rsprehn on Mar. 4, 2010, http://www.youtube.com/watch?v=OWiQQF4xQZc.

Tomed SomnoGuard FittingHeated for 20 seconds, YouTube video, uploaded to the Internet by britishsnoring on Apr. 26, 2010, http://www.youtube.com/watch?v=OXfN76M2I1A.

Wearing your Jaw Dynasplint® System, YouTube video, uploaded to the Internet by dynasplint on Oct. 5, 2011, http://www.youtube.com/watch?v=3hjP24aByd4.

"Tired of Your CPAP?", Houston Chronicle, Jan. 16, 2011.

PCT, "Invitation to Pay Additional Fees and, Where Applicable, Protest Fee", and extra sheets, mailed Jul. 25, 2012 from the European Patent Office acting as International Searching Authority.

PCT/US2012/036474 International Search Report, 6 pages, Sep. 9, 2012.

PCT/US2012/036474 Written Opinion of the International Searching Authority, 12 pages, Sep. 9, 2012.

FDA 510(k) Summary K061688, Sep. 8, 2006.
FDA 510(k) Summary K962516, Sep. 10, 1996.
FDA 510(k) Summary K033822, Feb. 6, 2004.
FDA 510(k) Summary K033823, Feb. 6, 2004.
FDA 510(k) Summary K972061, Aug. 21, 1997.
FDA 510(k) Summary K042161, Oct. 27, 2004.

Bailey, Premarket Notification [510(k)] Summary K013049 for mandibular repositioning appliance (device) known as NOrAD(TM), clearance granted by United States FDA, Nov. 29, 2001.

Bailey, Premarket Notification [510(k)] Summary K020893 for mandibular repositioning appliance (device) known as NOrAD(TM), clearance granted by United States FDA, May. 28, 2002.

Ranir, LLC, 510(k) Summary K1021118 for Intraoral Anti-Snoring Device known as Snore Guard Advance(TM), clearance granted by United States FDA, Sep. 8, 2010.

Sybron Dental Specialties, 510(k) Summary K070327 for Intraoral Devices for Snoring and Intraoral Devices for Snoring and Obstructive Sleep Apnea known as Removable Acrylic Herbst(TM), Allesee Snore Appliance(TM), and Enoch Snorinator(TM), clearance granted by United States FDA, May 25, 2007.

Hoffstein, "Review of oral appliances for treatment of sleep-disordered breathing", Sleep Breath (2007) 11:1-22, published online Nov. 29, 2006, Springer-Verlag.

Pancer et al., "Evaluation of Variable Mandibular Advancement Appliance for Treatment of Snoring and Sleep Apnea", Chest (1999); 116:1511-1518.

Randerath et al., "Non-CPAP therapies in obstructive sleep apnoea", Eur Respir J (2011); 37: 1000-1028.

* cited by examiner

ORAL DEVICES, KITS, AND METHODS FOR REDUCING SLEEP APNEA, SNORING, AND/OR NASAL DRAINAGE

Applicant claims, under 35 U.S.C. §119(e), the benefit of the filing date of Applicant's previously filed provisional application Ser. No. 61/488,021, filed May 19, 2011, which is incorporated herein by reference in its entirety.

BACKGROUND INFORMATION

1. Technical Field

The present disclosure relates to oral devices, apparatus, kits, and methods for reducing or eliminating obstructive sleep apnea, snoring and/or nasal drainage in mammals.

2. Background Art

Sleep apnea is a reduction in the blood oxygen level due to any cause. The present disclosure relates to "obstructive sleep apnea", which is problematic for many people—about 12 to 18 million people in the United States as of 2008. Obstructive sleep apnea (OSA) involves a reduction in breathing, called hypopneas, or a complete halt in airflow, called apneas, during sleep. Most pauses last 10 to 30 seconds, but some may persist for one minute or longer, according to the American Academy of Sleep Medicine. See Landers, S J, "*Link strengthened between sleep apnea and mortality risk*", amed-news, Sep. 1, 2008. As indicated in this article, apnea has been linked to higher mortality risks.

There are of course many known devices which claim to reduce or eliminate OSA, and these devices typically fall in two categories: external masks, such as the CPAP (continuous positive airway pressure) masks; and oral devices, sometimes referred to as mandibular splints. Pharmaceuticals comprise another category. The present disclosure involves the oral device or mandibular splint category.

Another discomfort is nasal or sinus drainage, sometimes referred to as nasal or sinus congestion, nasal or sinus drip, nasal or sinus irritation. The term "nasal drainage" is used herein to include all of these conditions unless otherwise noted. Non-oral products, such as adhesive strips positioned on the nose, may relieve some of these symptoms. However, nasal strips may only reduce anterior (frontal) congestion, and not posterior (throat) congestion.

Many of the known oral devices are uncomfortable and/or complicated, leading to reduced use. Furthermore, their use in humans may reduce speaking substantially, or at least the ability to speak understandably. A long felt and unmet need remains for an oral device, apparatus or kit, and methods of using these, to efficiently, safely and comfortably reduce or prevent OSA, snoring, and/or nasal drainage.

SUMMARY

In accordance with the present disclosure, oral devices, apparatus and kits are presented, as well as methods of using same, which reduce or overcome one or more of the problems of obstructive sleep apnea, snoring and other loss of sleep issues, and/or nasal drainage.

A first aspect of the disclosure is an apparatus (the words "apparatus" and "oral device" are used interchangeably herein) comprising:

an upper generally arched-shaped member that fits adjacent at least a portion of interior and exterior surfaces of a user's upper dentition;

a lower generally arched-shaped member that fits adjacent at least a portion of interior and exterior surfaces of a user's lower dentition;

wherein either the upper generally arch-shaped member comprises a molar extension projecting generally perpendicularly away from the upper generally arch-shaped member, so that when the user bites, the extension impinges on the lower generally arch-shaped member in a molar area, or the lower generally arch-shaped member comprises a molar extension projecting generally perpendicularly away from the lower generally arch-shaped member, so that when the user bites, the extension impinges on the upper generally arch-shaped member; and the upper and lower generally arch-shaped members having an anterior shape to form a gap sufficient for at least a portion of the user's tongue to extend forward into the gap.

A second aspect of the disclosure is an apparatus or oral device comprising:

an upper generally arched-shaped member that fits adjacent at least a portion of interior and exterior surfaces of a user's upper dentition;

a lower generally arched-shaped member that fits adjacent at least a portion of interior and exterior surfaces of a user's lower dentition;

the lower generally arch-shaped member comprising a lower molar extension projecting generally perpendicularly away from the lower generally arch-shaped member;

the upper generally arch-shaped member comprising an upper molar extension projecting generally perpendicularly away from the upper generally arch-shaped member and generally toward the molar extension of the lower generally arch-shaped member so that when the user bites the molar extensions impinge on one another in substantially overlapping fashion; and the upper and lower generally arch-shaped members having an anterior shape to form a gap sufficient for at least a portion of the user's tongue to extend forward into the gap.

A third aspect of the disclosure is an apparatus or oral device comprising:

an upper generally arched-shaped member that fits adjacent at least a portion of interior and exterior surfaces of a user's upper dentition;

a lower generally arched-shaped member that fits adjacent at least a portion of interior and exterior surfaces of a user's lower dentition;

the lower generally arch-shaped member comprising a lower right molar extension and a lower left molar extension, the lower right and lower left molar extensions projecting generally perpendicularly away from the lower generally arch-shaped member;

the upper generally arch-shaped member comprising an upper right molar extension and an upper left molar extension, the upper right and upper left molar extensions projecting generally perpendicularly away from the upper generally arch-shaped member and generally toward the lower right and lower left molar extensions, respectively, so that when the user bites or clenches, the molar upper right and lower right molar extensions impinge on one another in substantially overlapping fashion and the molar upper left and lower left molar extensions impinge on one another in substantially overlapping fashion;

the upper and lower generally arch-shaped members having an anterior shape to form a gap sufficient for at least a portion of the user's tongue to extend forward into the gap; and wherein each molar extension comprises at least one magnet.

Any of the apparatus described herein may be part of a kit comprising one or both upper and lower generally arch-shaped members substantially as described herein, in certain embodiments packaged in a carrying case.

A fourth aspect of the disclosure is a method comprising:
a) inserting at least one of an upper and/or a lower generally arch-shaped members into a users mouth and onto one or both of the upper and lower dentitions; and
b) wearing one or both of the upper and lower dentitions for a time sufficient to reduce one or more conditions selected from the group consisting of sleep apnea, snoring, and nasal drainage,
wherein the either the upper, the lower, or both generally arch-shaped members have right and left molar extensions, the molar extensions projecting generally perpendicularly away from the respective generally arch-shaped members, so that when the user bites, the extensions impinge on opposing generally arch-shaped members in a molar area or opposing molar extensions, the upper and lower generally arch-shaped members having an anterior shape to form a gap sufficient for at least a portion of the user's tongue to extend forward into the gap, wherein each molar extension optionally comprises at least one magnet.

Certain methods may comprise adjusting one or both arch-shaped members to comfortably fit the user's upper and/or lower dentitions.

Further aspects and advantages of apparatus and methods of the present disclosure will become apparent by reviewing the detailed description that follows.

Figure 1:
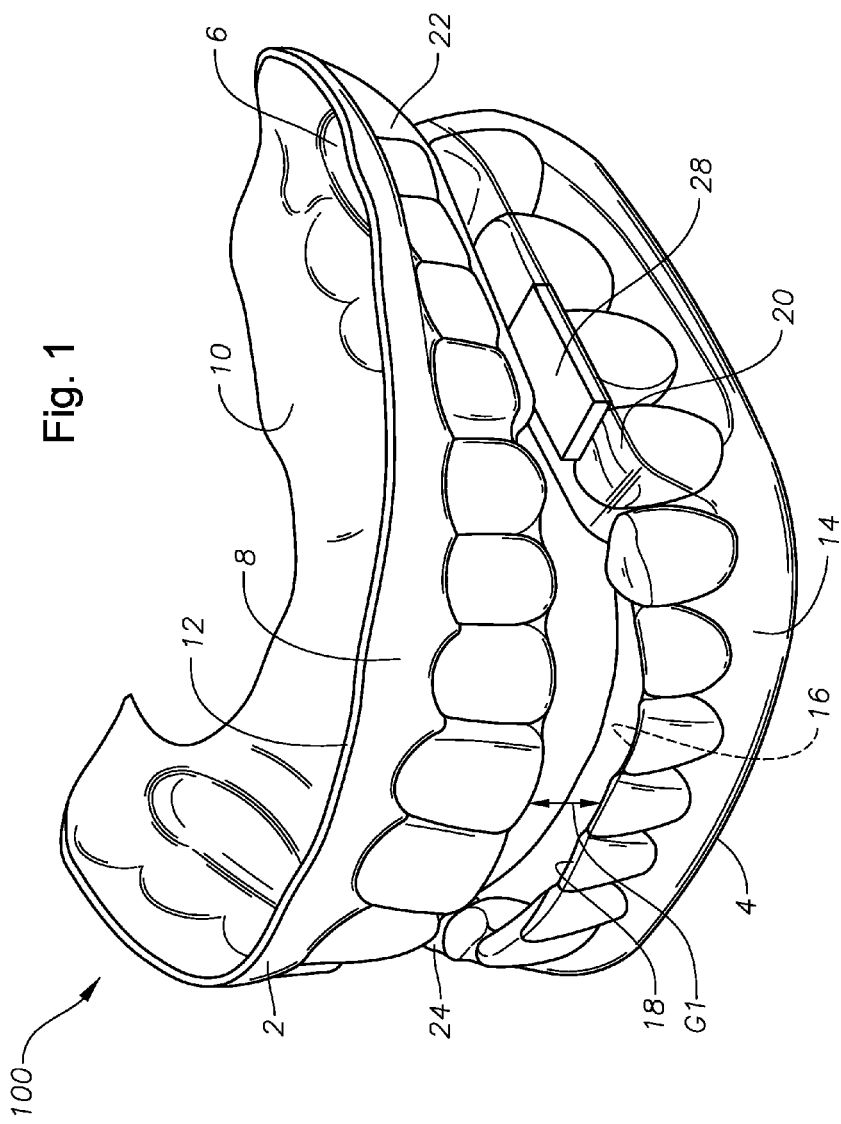
FIGS. 1, 2, and 3 are various views of one apparatus or kit embodiment within the present disclosure.

It is to be noted, however, that the appended drawings are not to scale and illustrate only typical embodiments of this disclosure, and are therefore not to be considered limiting of its scope, for the apparatus, kits, and methods of the disclosure may admit to other equally effective embodiments. Identical reference numerals are used throughout the several views for like or similar elements.

DETAILED DESCRIPTION

In the following description, numerous details are set forth to provide an understanding of the disclosed oral devices, kits and methods of their use. However, it will be understood by those skilled in the art that the oral devices, kits, and methods covered by the claims may be practiced without these details and that numerous variations or modifications from the specifically described embodiments may be possible and are deemed within the claims. All U.S. published patent applications and U.S. patents referenced herein are hereby explicitly incorporated herein by reference. In the event definitions of terms in the referenced patents and applications conflict with how those terms are defined in the present application, the definitions for those terms that are provided in the present application shall be deemed controlling.

As used herein the phrase "generally arched-shaped" means the shape of a member resembles an arch in the same way that the upper and lower teeth of a user resemble arches. The phrase "adjacent at least a portion of interior and exterior surfaces", as that term is used herein when referring to the generally arch-shaped members, means that the generally arch-shaped members are adjacent to and touching at least one surface of the upper or lower teeth concerned, but some "looseness" is allowed, so that the members may move away from the teeth slightly, for example if the material of the member stretches or deforms, such as during insertion into or removal from the mouth. As used herein the term "user" means a human or other mammal that employs an apparatus of this disclosure in its mouth. The term "subject" may also be used and is considered interchangeable with the term "user."

The present disclosure relates generally to apparatus, kits, and methods for reducing or eliminating sleep and other disorders, and more specifically to apparatus for reducing or eliminating obstructive sleep apnea (OSA), snoring, and/or nasal drainage. A particular use for apparatus and kits of this disclosure is for humans, but they may also be used for other mammals. Certain embodiments may also be used as athletic mouth guards for upper, lower, or both dentitions.

In certain embodiments, the gap (denoted G1 in the various figures) may have a distance ranging from about 1 to about 20 mm, or from about 5 to about 15 mm.

The lateral length (L1 in FIG. 7) of the upper and lower molar extensions, i.e., the distance along the molar teeth, may be 10 mm or more, or may range from 10 to about 50 mm or from about 12 to about 24 mm. In certain embodiments having an offset, the length of the upper and the lower molar extensions may each be about one half of these lengths. In certain embodiments, a goal is to keep the upper and lower molar extensions as short as possible to maintain the gap as large as possible.

Figure 8:
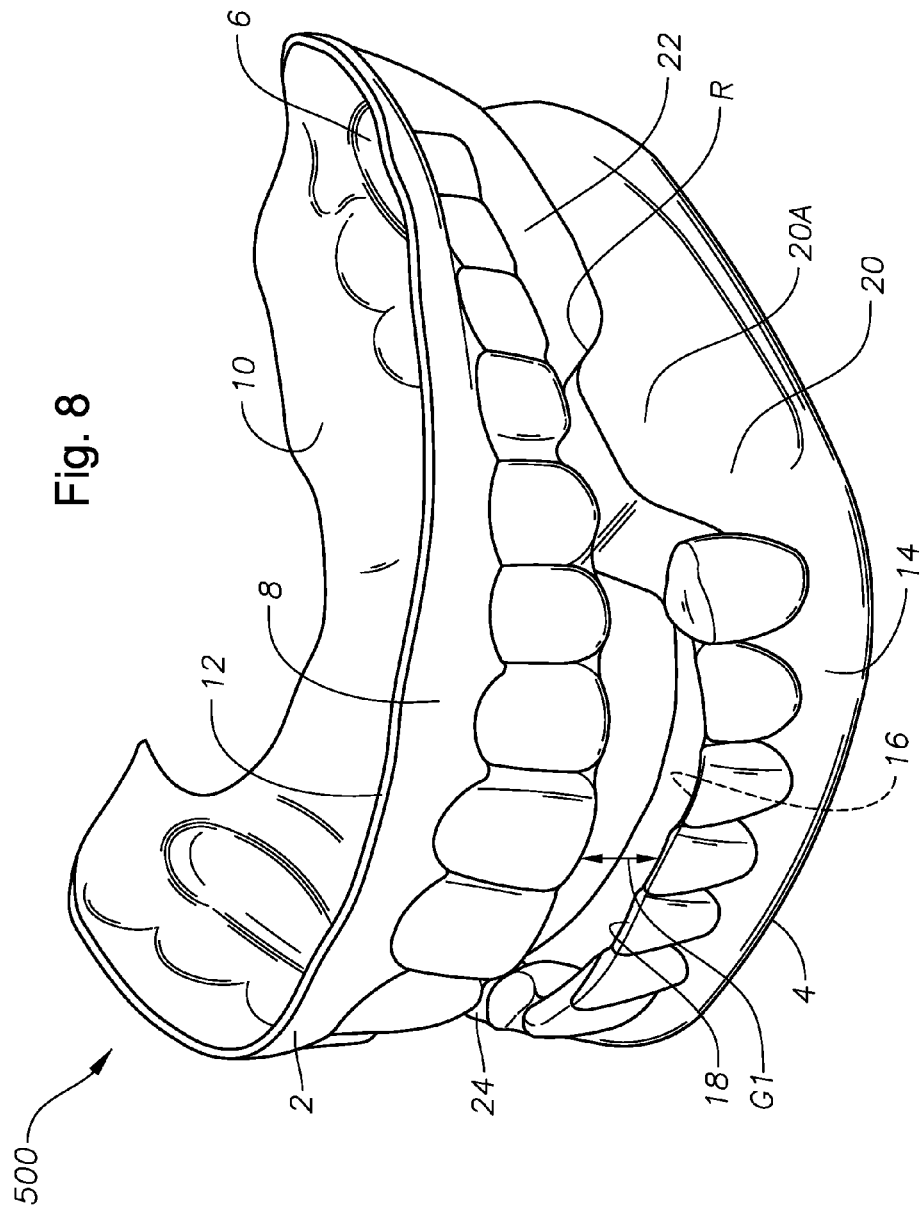
FIGS. 8, 9, and 10 illustrate schematically various views of another apparatus or kit embodiment in accordance with the present disclosure.
Figure 9:
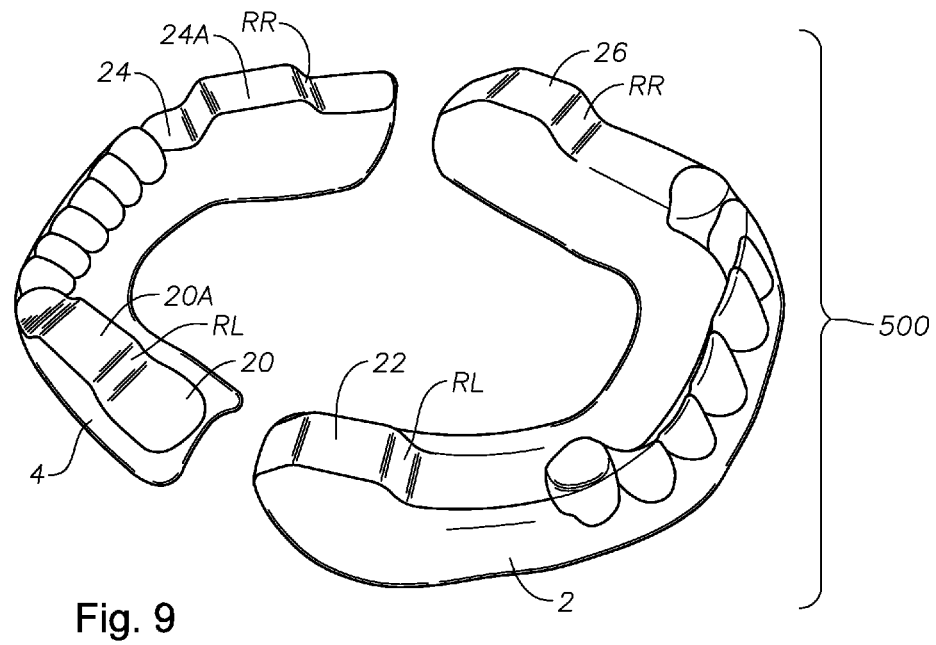
Figure 10:
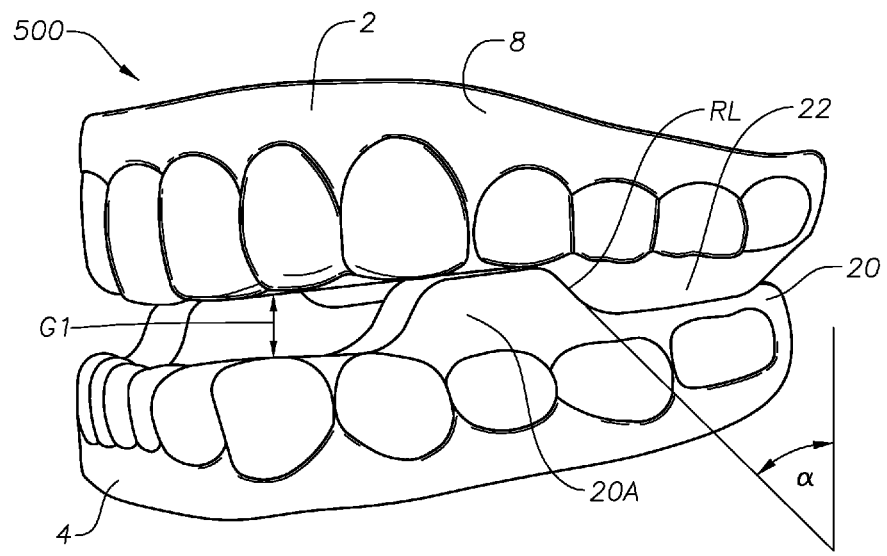

In certain embodiments the molar extensions may have a vertical length (L2 in FIG. 7) of 20 mm or less, in certain embodiments 16 mm or less. The average vertical distance of upper and lower molar extensions in non-offset embodiments is about 10 mm (5 mm for upper, 5 mm for lower molar extensions). In certain embodiments that may have an "offset", such as may be provided by left and right-side ramps as illustrated in FIGS. 8, 9, and 10, the upper or lower molar extensions may comprise the entire vertical length (i.e., all 10 mm may in certain embodiments be in the upper molar extensions; in certain other embodiments the entire 10 mm may be in the lower molar extensions). In certain embodiments within the first aspect the upper generally arch-shaped member comprises two upper molar extensions, one extending from a right-side upper molar region, and the second extending from a left-side upper molar region. Similarly, in certain embodiments within the second aspect the upper generally arch-shaped member comprises two lower molar extensions, one extending from a right-side lower molar region, and the second extending from a left-side lower molar region.

In certain embodiments the upper and lower members each may comprise a moldable material selected from the group consisting of synthetic and natural materials. Synthetic materials may be selected from the group consisting of polymeric materials, as further discussed herein. In certain apparatus the arch-shaped members and the molar extensions comprise a polymeric material.

In certain embodiments, each molar extension may comprise at least one magnet. In certain embodiments the magnets are embedded in the polymeric material of the molar extensions. In certain embodiments, an upper right magnet has polarity opposite that of a lower right magnet, and an upper left magnet has a polarity opposite that of a lower left magnet. In certain embodiments, the magnets may be flat shaped and embedded into the plastic of the molar extensions. In certain embodiments, such as illustrated in FIG. 4, the flat-shaped magnets may have a north pole on one of their major surfaces and a south pole on its other major surface.

Figure 2:
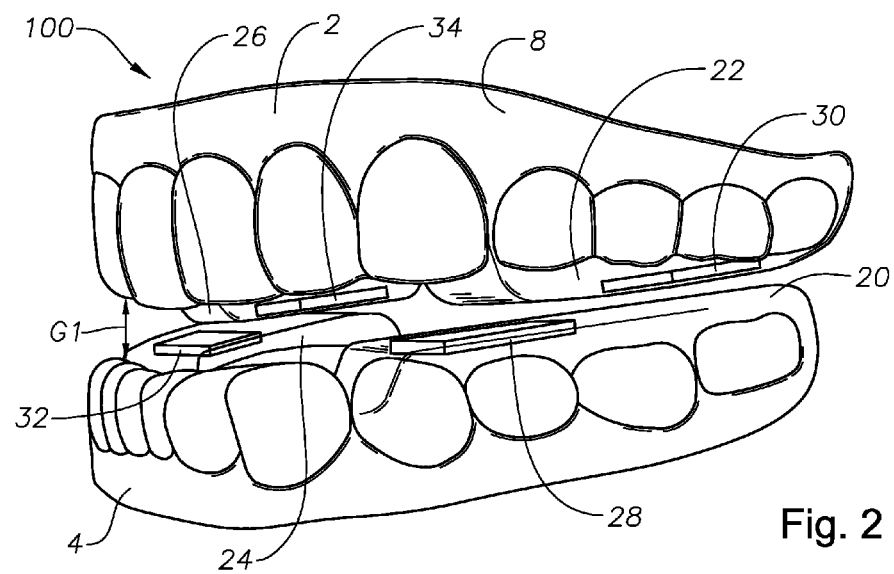

Referring to FIGS. 1 and 2, there is illustrated schematically a perspective view of one apparatus 100 in accordance with the disclosure. Apparatus embodiment 100 includes an upper generally arch-shaped member 2 and a lower generally arch-shaped member 4. Upper generally arch-shaped member 2 includes an exterior wall 8 and an interior wall 10, custom-shaped for the user's upper dentition, and which together define a trough 6 for friction fitting adjacent the upper dentition of a user. An upper connecting portion 12 connects exterior wall 8 and interior wall 10. Connecting portion 12 may be rather thin or pointed in the area of the front teeth, and rather flat or planar in the area of the back molar teeth. Similarly, lower generally arch-shaped member 4 includes an exterior wall 14, and an interior wall 16, the latter being mostly hidden in the views of FIGS. 1 and 2. A lower connecting portion 18 connects walls 14 and 16, and as with upper connecting portion 12, lower connecting portion 18 may be rather thin or pointed near the front teeth of the user, and rather flat or planar near the lower molars of the user.

Figure 3:
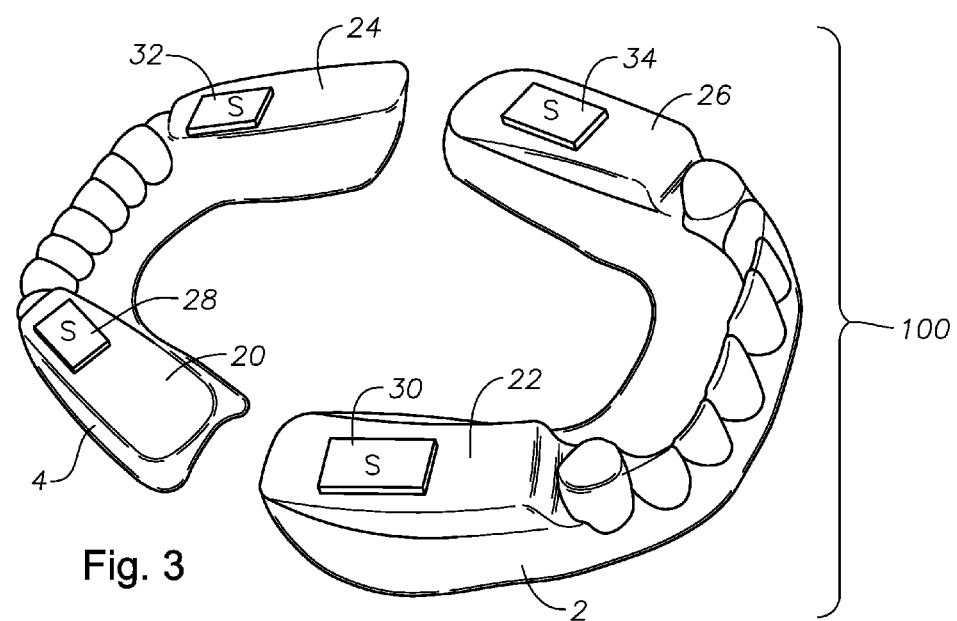

As perhaps more clearly viewed in FIG. 2, embodiment 100 includes a lower left molar extension 20 and an upper left molar extension 22, each extending generally perpendicularly away from their respective members. FIG. 3 illustrates schematically upper generally arch-shaped member 2 in a 180 degree flip from its "in use" position to more clearly illustrate a lower right molar extension 24 and an upper right molar extension 26. FIG. 3 also allows viewing of flat-shaped magnets 28, 30, 32 and 34 fully embedded in their respective molar extensions. Members 2 and 4, as well as molar extensions 20, 22, 24, and 26 comprise the same moldable polymeric material in this embodiment.

Figure 4:
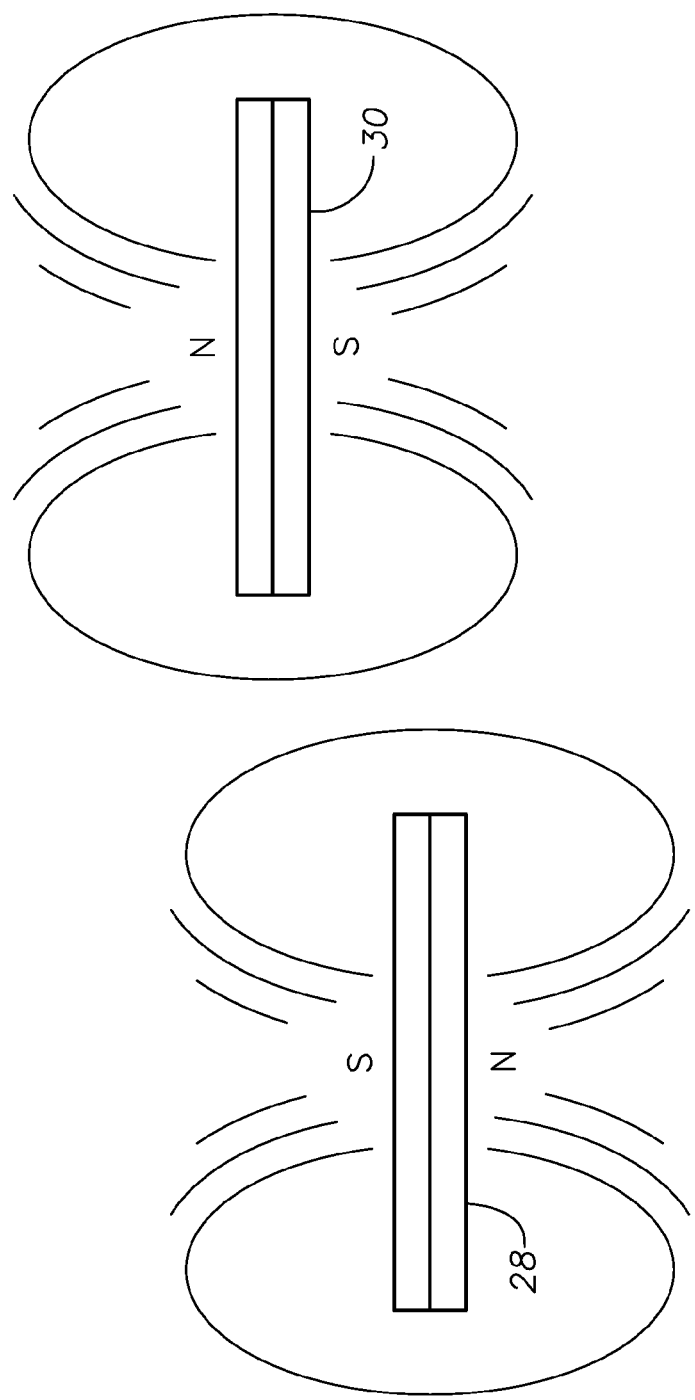
FIG. 4 is a schematic side elevation view of an arrangement of magnets useful in the apparatus or kit illustrated schematically in FIGS. 1-3.

As generally may be seen in FIGS. 2 and 3, and more specifically illustrated in the schematic diagrams in FIG. 4, magnets 28 and 30 have, in this embodiment, a specific spatial relationship. The respective north and south poles of these magnets are arranged so that when placed as viewed in FIG. 4, they will substantially repel one another by virtue of their respective magnetic field lines being unable to cross, forcing the mandible down and forward. Magnets 32, 34 may have the same spatial and magnetic relationship. As this occurs, embodiment 100 will tend to keep a user's airway open by creating a gap between upper portion 2 and lower portion 4, near the front teeth, as indicated by double-headed arrow G1 in FIGS. 1 and 2.

Figure 2A:
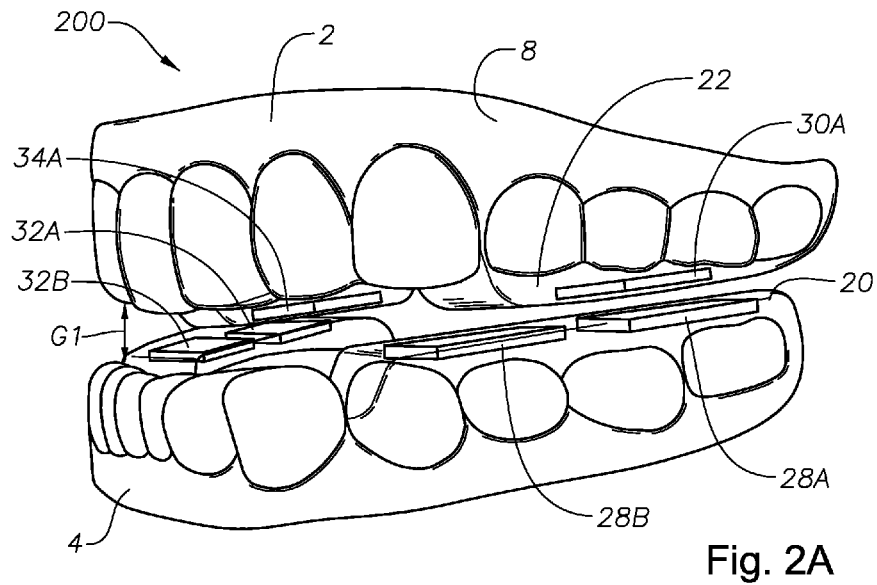
FIGS. 2A and 2B are views of another apparatus or kit embodiment within the present disclosure.
Figure 2B:
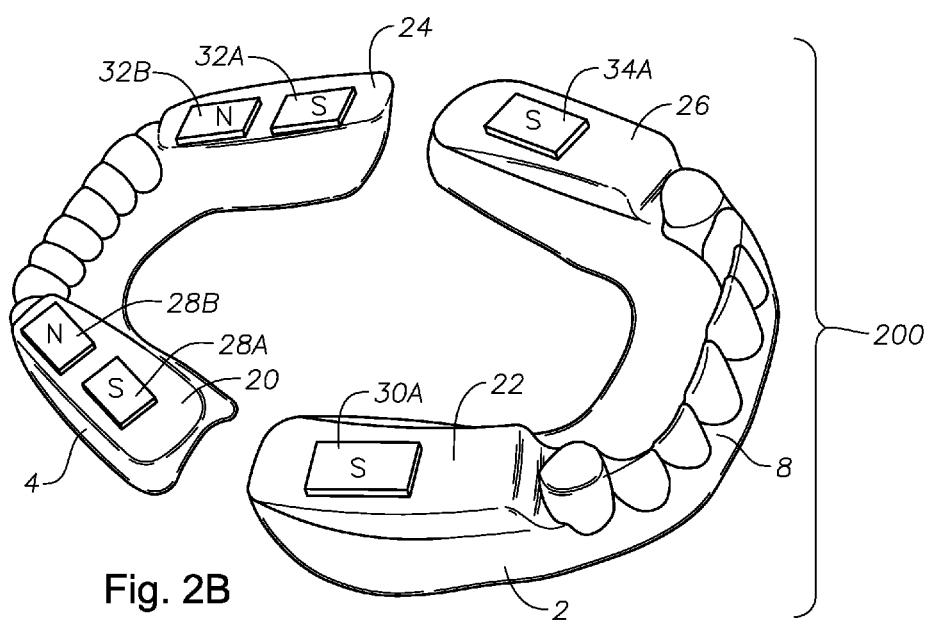

FIGS. 2A and 2B are views of another apparatus or kit embodiment 200 within the present disclosure. In embodiment 200, magnets 28A, 28B, 30A, 32A, 32B, and 34A are all embedded in their respective molar extensions. In embodiment 200, magnet 28A has a south pole facing away from left lower molar extension 20, and a north pole facing left lower molar extension 20. Magnet 28B has a south pole facing left lower molar extension 20, and a north pole facing away from left lower molar extension 20. Also in embodiment 200, magnet 32A has a south pole facing away from right lower molar extension 24, and a north pole facing right lower molar extension 24. Magnet 32B has a south pole facing right lower molar extension 24, and a north pole facing away from right upper molar extension 24. Magnet 34A has a south pole facing away from right upper molar extension 26, and a north pole facing toward right upper molar extension 26. Magnet 30A has a south pole facing away from left upper molar extension 22, and a north pole facing toward left upper molar extension 22. It is noted that the magnetic poles of each magnet could be reversed to arrive at substantially the same embodiment. In both embodiment 200 and its "reverse" poles sister embodiment, there will be magnetic attraction between magnets 28B and 30A, as well as between magnets 32B and 34A, while there will be a slight magnetic repulsion between magnets 32A and 34A, as well as between magnets 28A and 30A. In this embodiment and others like it, the magnetic attraction and repulsion thus may be adjusted depending on the particular user, for example the strength of the user's jaw muscles.

Figure 3A:
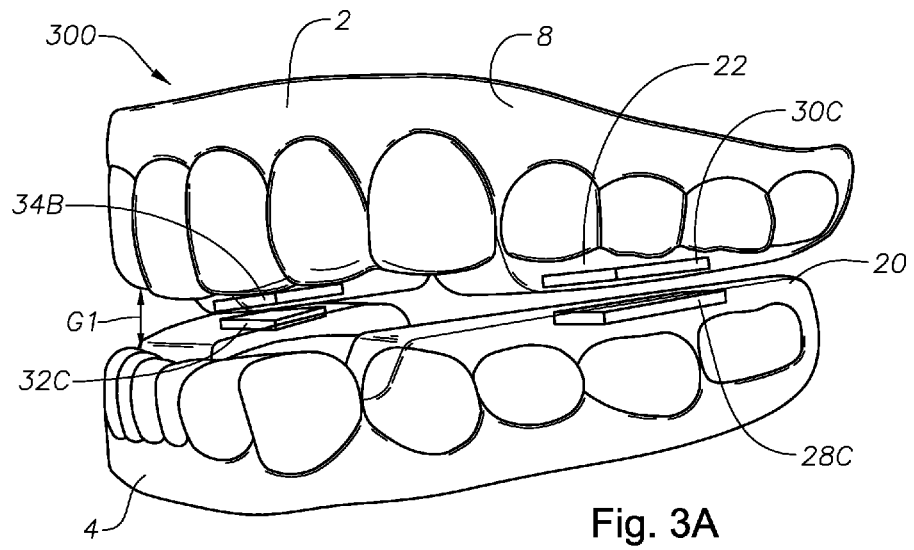
FIGS. 3B and 3B are views of another apparatus or kit embodiment within the present disclosure.
Figure 3B:
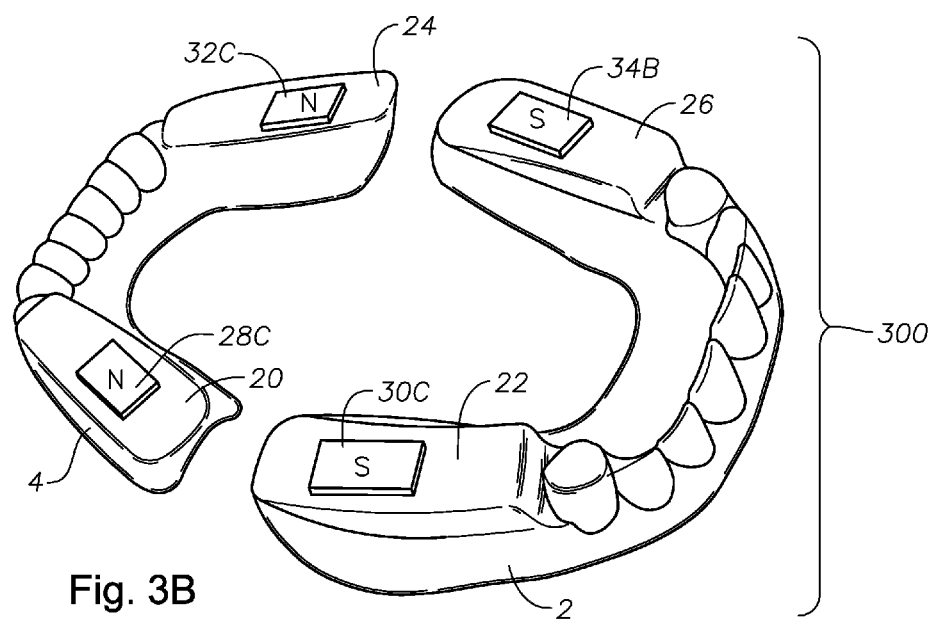

FIGS. 3A and 3B are views of another apparatus or kit embodiment 300 within the present disclosure. In embodiment 300, magnets 28C, 30C, 32C, and 34B are all embedded in their respective molar extensions. In embodiment 300, magnet 28C has a south pole facing toward left lower molar extension 20, and a north pole facing away from left lower molar extension 20. Magnet 32C has a south pole facing right lower molar extension 24, and a north pole facing away from right lower molar extension 24. Also in embodiment 300, magnet 30C has a south pole facing away from left upper molar extension 22, and a north pole facing left upper molar extension 22. Magnet 34B has a south pole facing away from right upper molar extension 26, and a north pole facing right upper molar extension 26. Magnet 34C has a south pole facing away from right upper molar extension 26, and a north pole facing right upper molar extension 26. It is noted that the magnetic poles of each magnet could be reversed to arrive at substantially the same embodiment. In both embodiment 300 and its "reverse" poles sister embodiment, there will be magnetic attraction between magnets 28C and 30C, as well as between magnets 32C and 34B. In this embodiment and others like it, the magnetic attractions may be adjusted depending on the particular user, for example the strength of the user's jaw muscles, by adjusting the strength of the magnets.

Figure 5:
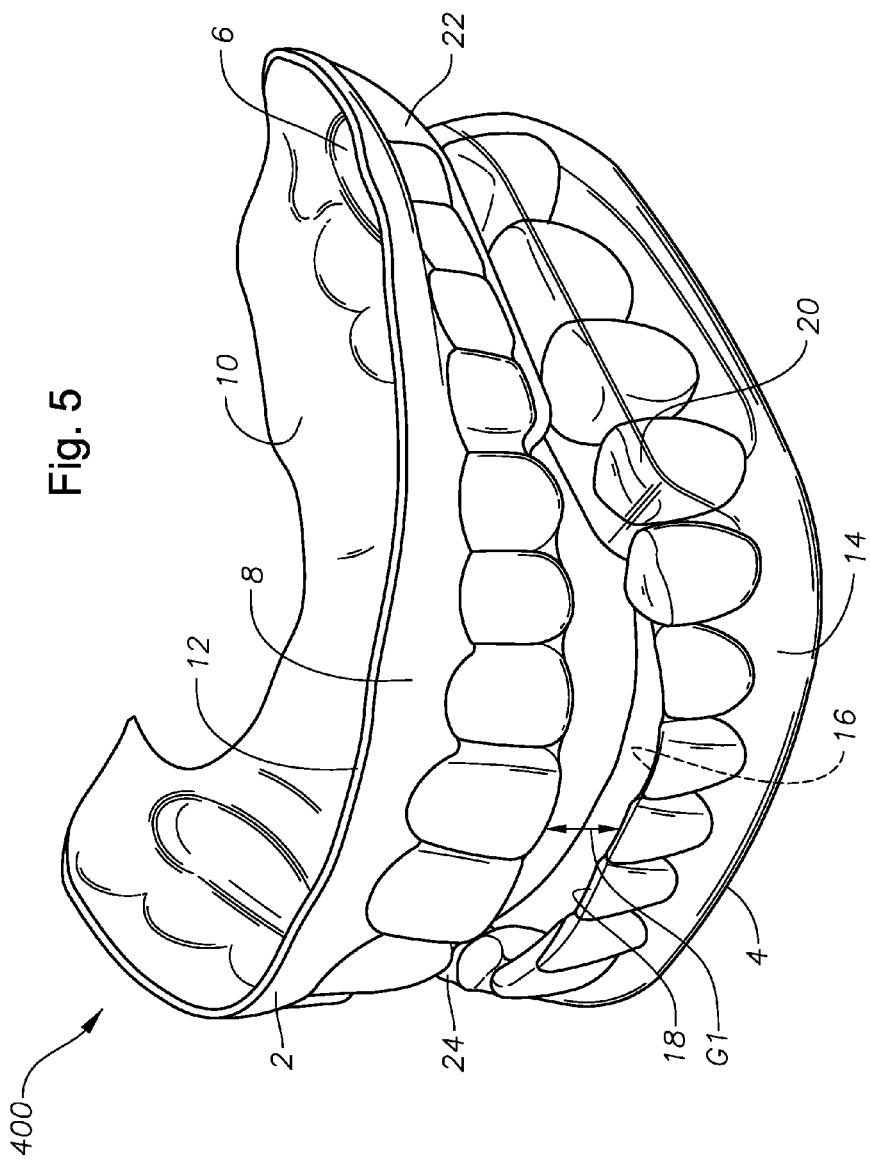
FIGS. 5, 6, and 7 illustrate schematically various views of another apparatus or kit embodiment in accordance with the present disclosure.
Figure 6:
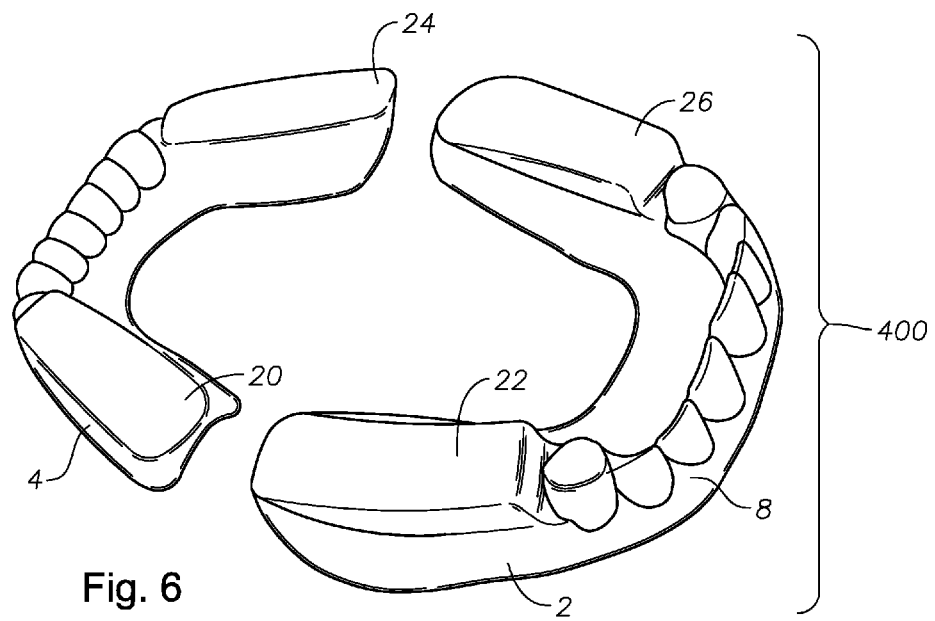
Figure 7:
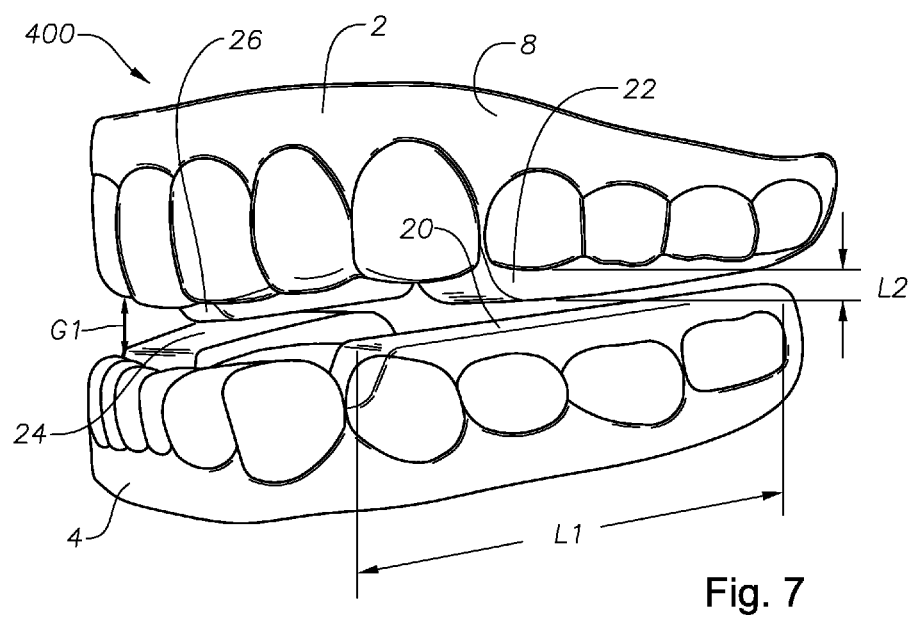

FIGS. 5, 6, and 7 illustrate schematically various views of another apparatus embodiment 400 in accordance with the present disclosure, which is the same as embodiment 100 but without magnets. FIG. 7 illustrates lengths L1 and L2, as well as gap G1.

FIGS. 8, 9, and 10 illustrate schematically various views of another apparatus or kit embodiment 500 in accordance with the present disclosure, illustrating an offset or ramp R between upper portion 2 and lower portion 4 created by a left ramp area (RL) and a right ramp area (RR). A tapered lower anterior left molar extension 20A may slidingly move adjacent a matching tapered upper posterior left molar extension 22 in the area of left ramp area RL, where faces of components 20A and 22 may slide against each other at an angle α (FIG. 10). Similarly on the right side, a tapered lower anterior right molar extension 24A may slidingly move adjacent a matching tapered upper posterior right molar extension 26 (not viewable in FIGS. 8 and 10, but illustrated in exploded view of FIG. 9). Ramps RL and RR create a tendency for the lower portion 4 to move downward as lower portion 4 moves back toward the user's throat. Movement of the lower jaw backwards is a natural movement during sleep. As this occurs, embodiment 500 will tend to keep the airway open by creating a gap between upper portion 2 and lower portion 4, near the front teeth, as indicated by double-headed arrow G1 in FIG. 1. This gap may be important in methods of reducing nasal drainage, perhaps more important than forward movement of the lower jaw.

The materials of construction of the upper and lower members may comprise any moldable plastic (polymeric) material that is approved for use in oral medical devices and appliances for human use and that may be custom fitted for each user and tooth-retained via friction grip, and materials approved for animal use. The members may comprise a single material, or combination of materials. The members may comprise more than one layer of material, and each layer may be the same or different. The polymeric materials may be filled with various fillers, extenders, pigments, and other additives. Suitable polymeric materials include thermoplastics, thermosetting polymers, elastomers, and thermoplastic elastomers. The polymeric materials may comprise co-polymers, ter-polymers, and blends of two or more chemical types of polymers, or blends of two or more polymers of the same chemical type, for example, a blend of two thermoplastics having different molecular weights.

Examples of specific polymers include polyacrylics, polyvinyls, polyvinyl alcohols, and the like. An example of a suitable polymeric material is a durable fade-proof acrylic that retains its shape and color for at least four-five years. Another example is made of a very pliable, soft, custom-injected silicone. Another example is a polymeric material compatible with home/office based bleaching techniques, such as the material used to make an OSAP device, and materials that can be molded into a ready-made semi-universal trial version, which may be suitable for patients who cannot endure having their impressions taken. In addition, the trial version is an inexpensive way to test a particular patients' tolerance to oral therapy. Another example is the material used in the device known under the trade designation SAGA. This device consists of a hard acrylic shell laminated to a soft vinyl liner. Another example is the acrylic material (Bruxeze™) that softens in hot water to provide a combination of comfort, strength, and retention, and which is used in the Adjustable PM Positioner™, an appliance that fits over all maxillary and mandibular teeth. Another example are the materials used in the device known as SomnoGuard® AP, which consists of an upper and a lower tray each made of two materials. The outer tray shells consist of solid clear and transparent medical grade polycarbonate. The inner lining which accommodates the teeth impressions is made of a thermoplastic copolymer. After the oral appliance is heated in a hot water bath its thermoplastic body molds easily to the teeth and jaws allowing any medical doctor to fit the device chair side. Yet another example is the material employed in the device known as SomnoGuard AP Pro®, which is a dental lab made two-part mandibular adjustable positioner to treat snoring and mild to moderate sleep apnea, and comprises common acrylic/elastomeric thermoform dental materials available in any dental lab after taking impressions of the lower and upper jaws and producing plaster models. Other polymeric materials that may be useful include nitinol, silicone, a PET, or any other biocompatible polymeric material. Other possible examples include PTFE, e-PTFE, polypropylene, polyurethane, polycarbonate, polyethylene terephthalate, stainless steel, titanium, tantalum, gold, polyvinidylene fluoride and combinations thereof.

The molar extensions may either be molded using special molds, or built up by applying a paste or solution of polymeric precursor materials and swabbing the precursors materials on the appropriate areas. In certain embodiments, this may need to be done repeatedly to build up the molar extension to functional length.

Magnets which may be useful in apparatus of this disclosure include rare earth magnets, such as samarium-cobalt and neodymium-iron-boron magnets. It has become possible to produce magnets with small enough dimensions for dental applications and yet still provide the necessary forces. Certain embodiments may employ magnets of the "closed field" type. In this type of system, a soft magnetic or ferromagnetic material, such as ferritic or martensitic stainless steel or Pd—Co—Ni alloy, is implanted into the jaw, rather than a magnet, to provide attractive force to hold the denture in place. This implant is known as a "keeper". In this configuration, the magnetic field lines are shunted through the keeper as it is the path of minimum energy and there is no magnetic field experienced in the oral cavity. U.S. Pat. Nos. 6,659,771, 5,678, 998, 5,013,243 and 6,299,450 describe small yet powerful magnets for cooperating with a non-magnet implanted "keeper" for denture attachment. The non-magnet keeper is made of a magnet-attracted material, such as a soft magnetic or ferromagnetic material, but is not a permanent magnet. U.S. Pat. No. 4,396,373 describes a removable orthodontic appliance having two permanent magnets carried by two caps, respectively, having facing poles which are in registry when the mouth is normally closed, exerting a magnetic force in a direction substantially normal to the occlusal plane. The opposing magnets have confronting poles with like-polarity such that the magnets repel and develop intrusive forces upon the respective teeth. U.S. Pat. No. 4,671,767 discloses both fixed and removable orthodontic devices that use magnets. The magnets are secured to removable or fixed orthodontic devices and are positioned bilaterally in the posterior molar regions. The faces of the magnets are oriented such that they repel each other, thereby creating magnetic forces parallel to the occlusal plane for urging the mandible forward.

According to U.S. Pat. No. 7,712,468, which discloses a removable magnetic dental appliance, the magnetic orthodontic devices described above employ "open field" magnetic configurations, which are potentially harmful to the local tissues in the oral cavity, especially since the devices are designed for long-term use. Furthermore, the appliances are uncomfortable to wear.

Any of the magnets discussed in these patent and publications would be useable in apparatus and kits disclosed herein.

If desired, fastening means may be employed to fasten one or more of the members in the users mouth. Hook and loop fasteners are common and require no further explanation. One preferred hook and loop fastener is that known under the trade designation Velcro®, available from Velcro USA, Manchester, N.H.

Although the foregoing description is intended to be representative of apparatus, kits, and methods in accordance with the present disclosure, it is not intended to in any way limit the scope of the appended claims.

What is claimed is:

1. An apparatus comprising:
   an upper generally arched-shaped member that is configured to fit adjacent at least a portion of interior and exterior surfaces of a user's upper dentition, the upper generally arched-shaped member comprising a moldable polymeric material;
   a lower generally arched-shaped member of the same moldable polymeric material that is configured to fit adjacent at least a portion of interior and exterior surfaces of the user's lower dentition;
   the lower generally arch-shaped member comprising an anterior lower right molar extension and an anterior lower left molar extension of the same moldable polymeric material, the anterior lower right and lower left molar extensions formed integrally with and projecting generally perpendicularly away from the lower generally arch-shaped member and generally toward the upper generally arch-shaped member;

the upper generally arch-shaped member comprising a posterior upper right molar extension and a posterior upper left molar extension of the same moldable polymeric material, the posterior upper right and upper left molar extensions formed integrally with and projecting generally perpendicularly away from the upper generally arch-shaped member and generally toward the lower generally arch-shaped member;

so that when the user bites or clenches, the posterior right and left upper molar extensions impinge on the lower generally arch-shaped member, and the anterior right and left lower molar extensions impinge on the upper generally arch-shaped member;

the upper and lower generally arch-shaped members having an anterior shape to form a gap sufficient for at least a portion of the user's tongue to extend forward into the gap without being impeded in forward movement by the apparatus;

wherein each of the lower and upper generally arch-shaped members comprises a plurality of magnets;

wherein the plurality magnets are embedded in the same moldable polymeric material;

wherein the posterior upper right molar extension comprises an upper right magnet and the anterior lower right molar extension comprises a lower right magnet, wherein the upper right and lower right magnets are each flat-shaped magnets each having first and second major surfaces, each magnet having a first pole on the first major surface thereof and a second pole on the second major surface thereof, and wherein the upper right and lower right magnets have repelling polarity when the apparatus is positioned in the user's mouth, and the posterior upper left molar extension comprises an upper left magnet and the anterior lower left molar extension comprises a lower left magnet, wherein the upper left and lower left magnets are each flat-shaped magnets each having first and second major surfaces, each magnet having a first pole on the first major surface thereof and a second pole on the second major surface thereof, wherein the upper left and lower left magnets have repelling polarity when the apparatus is positioned in the user's mouth.

2. An apparatus comprising:

an upper generally arched-shaped member configured to fit adjacent at least a portion of interior and exterior surfaces of a user's upper dentition, the upper generally arched-shaped member comprising a moldable polymeric material;

a lower generally arched-shaped member of the same moldable polymeric material configured to fit adjacent at least a portion of interior and exterior surfaces of the user's lower dentition;

the lower generally arch-shaped member comprising an anterior lower right molar extension and an anterior lower left molar extension of the same moldable polymeric material, the anterior lower right and lower left molar extensions formed integrally with and projecting generally perpendicularly away from the lower generally arch-shaped member;

the upper generally arch-shaped member comprising a posterior upper right molar extension and a posterior upper left molar extension of the same moldable polymeric material, the posterior upper right and upper left molar extensions formed integrally with and projecting generally perpendicularly away from the upper generally arch-shaped member and generally toward the lower generally arch-shaped member;

so that when the user bites or clenches, the posterior right and left upper molar extensions impinge on the lower generally arch-shaped member, and the anterior right and left lower molar extensions impinge on the upper generally arch-shaped member;

the upper and lower generally arch-shaped members having an anterior shape to form a gap sufficient for at least a portion of the user's tongue to extend forward into the gap without being impeded in forward movement by the apparatus;

wherein each of the lower and upper generally arched-shaped members comprises a plurality of magnets;

wherein the posterior upper right molar extension comprises an upper right magnet and the anterior lower right molar extension comprises first and second lower right magnets, wherein the upper right and lower right magnets are each flat-shaped magnets each having first and second major surfaces, each magnet having a first pole on the first major surface thereof and a second pole on the second major surface thereof, the posterior upper left molar extension comprises an upper left magnet and the anterior lower left molar extension comprises first and second lower left magnets, wherein the upper left and lower left magnets are each flat-shaped magnets each having first and second major surfaces, each magnet having a first pole on the first major surface thereof and a second pole on the second major surface thereof, and;

wherein, when the apparatus is positioned in the user's mouth, the upper right and the first lower right magnets have a repelling polarity, the upper right and the second lower right magnets have attracting polarity, and the upper right magnet is positioned substantially facing the first lower right magnet, and the upper left and the first lower left magnets have a repelling polarity, the upper left and the second lower left magnets have attracting polarity, and the upper left magnet is positioned substantially facing the first lower left magnet.

3. An apparatus comprising:

an upper generally arched-shaped member configured to fit adjacent at least a portion of interior and exterior surfaces of a user's upper dentition, the upper generally arched-shaped member comprising a moldable polymeric material;

a lower generally arched-shaped member of the same moldable polymeric material configured to fit adjacent at least a portion of interior and exterior surfaces of the user's lower dentition;

the lower generally arch-shaped member comprising an anterior lower right molar extension and an anterior lower left molar extension of the same moldable polymeric material, the anterior lower right and lower left molar extensions formed integrally with and projecting generally perpendicularly away from the lower generally arch-shaped member;

the upper generally arch-shaped member comprising a posterior upper right molar extension and a posterior upper left molar extension of the same moldable polymeric material, the posterior upper right and upper left molar extensions formed integrally with and projecting generally perpendicularly away from the upper generally arch-shaped member and generally toward the lower generally arch-shaped member;

so that when the user bites or clenches, the posterior right and left upper molar extensions impinge on the lower generally arch-shaped member, and the anterior right and left lower molar extensions impinge on the upper generally arch-shaped member;

the upper and lower generally arch-shaped members having an anterior shape to form a gap sufficient for at least a portion of the user's tongue to extend forward into the gap without being impeded in forward movement by the apparatus;

wherein each of the lower and upper generally arched-shaped members comprises a plurality of magnets;

wherein the posterior upper right molar extension comprises an upper right magnet and the anterior lower right molar extension comprises a lower right magnet, wherein the upper right and lower right magnets are each flat-shaped magnets each having first and second major surfaces, each magnet having a first pole on the first major surface thereof and a second pole on the second major surface thereof, the posterior upper left molar extension comprises an upper left magnet and the anterior lower left molar extension comprises a lower left magnet, wherein the upper left and lower left magnets are each flat-shaped magnets each having first and second major surfaces, each magnet having a first pole on the first major surface thereof and a second pole on the second major surface thereof, and wherein, when the apparatus is positioned in the user's mouth, the upper right and the lower right magnets have an attracting polarity, and wherein the upper right magnet is positioned substantially facing the lower right magnet, and the upper left and the lower left magnets have an attracting polarity, and wherein the upper left magnet is positioned substantially facing the lower left magnet.

* * * * *